US010768136B2

(12) United States Patent  
Kishioka et al.

(10) Patent No.: US 10,768,136 B2  
(45) Date of Patent: Sep. 8, 2020

(54) ELECTROLYTE CONCENTRATION MEASUREMENT DEVICE

(71) Applicant: HITACHI HIGH-TECHNOLOGIES CORPORATION, Tokyo (JP)

(72) Inventors: Atsushi Kishioka, Tokyo (JP); Tetsuyoshi Ono, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 0 days.

(21) Appl. No.: 16/319,839

(22) PCT Filed: Jun. 13, 2017

(86) PCT No.: PCT/JP2017/021856  
§ 371 (c)(1),  
(2) Date: Jan. 23, 2019

(87) PCT Pub. No.: WO2018/020880  
PCT Pub. Date: Feb. 1, 2018

(65) Prior Publication Data  
US 2019/0265187 A1    Aug. 29, 2019

(30) Foreign Application Priority Data

Jul. 26, 2016  (JP) ................................. 2016-146319

(51) Int. Cl.  
*G01N 27/333* (2006.01)  
*G01N 27/30* (2006.01)  
(Continued)

(52) U.S. Cl.  
CPC ............. *G01N 27/333* (2013.01); *G01N 1/00* (2013.01); *G01N 27/26* (2013.01); *G01N 27/301* (2013.01);  
(Continued)

(58) Field of Classification Search  
CPC ........ G01N 27/333; G01N 1/00; G01N 35/00; G01N 27/26; G01N 27/4166;  
(Continued)

(56) References Cited

U.S. PATENT DOCUMENTS 5,800,056 A    9/1998  Suzuki et al.  
2003/0057108 A1    3/2003  Sridharan  
(Continued)

FOREIGN PATENT DOCUMENTS

EP    2208989 A1    7/2010  
EP    2511699 A1    10/2012  
(Continued)

OTHER PUBLICATIONS

International Search Report dated Aug. 29, 2017 of International Application No. PCT/JP2017/021856.  
(Continued)

*Primary Examiner* — J. Christopher Ball  
(74) *Attorney, Agent, or Firm* — Volpe and Koenig, P.C.

(57) ABSTRACT

An electrolyte concentration measurement device includes a measurement unit that includes an ion selective electrode, a reference electrode and a potential measurement unit; a record and calculation unit that obtains an ion concentration of an internal standard liquid or a specimen; and a concentration value correction/determination unit that determines whether the ion concentration of the internal standard liquid is within a preset value range, and corrects an ion concentration value of the internal standard liquid obtained by the record and calculation unit, in which the measurement unit includes an internal standard liquid bottle storage unit storing a plurality of bottles, and the concentration value correction/determination unit corrects the obtained ion concentration of the internal standard liquid after the bottle is switched, by using information of the ion concentration (Continued)

before the bottle accommodating the internal standard liquid is switched.

5 Claims, 12 Drawing Sheets

(51) Int. Cl.
  *G01N 27/416* (2006.01)
  *G01N 27/26* (2006.01)
  *G01N 35/00* (2006.01)
  *G01N 1/00* (2006.01)
(52) U.S. Cl.
  CPC ......... *G01N 27/4166* (2013.01); *G01N 35/00* (2013.01)
(58) Field of Classification Search
  CPC ......... G01N 27/301; G01N 2035/1032; G01N 35/1009; G01N 35/1095; G01N 35/00584; G01N 2035/00534
  See application file for complete search history.

(56) References Cited

U.S. PATENT DOCUMENTS

| | | |
|---|---|---|
| 2012/0177536 A1 | 7/2012 | Sakei et al. |
| 2012/0261260 A1 | 10/2012 | Li et al. |

FOREIGN PATENT DOCUMENTS

| | | | |
|---|---|---|---|
| JP | 60-148965 | U | 10/1985 |
| JP | 04-138365 | A | 5/1992 |
| JP | 2503751 | Y2 | 4/1996 |
| JP | 08-220049 | A | 8/1996 |
| JP | 08-304411 | A | 11/1996 |
| JP | 09-033538 | A | 2/1997 |
| JP | 09-325150 | A | 12/1997 |
| JP | H09-325150 | A * | 12/1997 |
| JP | 2003-516549 | A | 5/2003 |
| JP | 2004-251799 | A | 9/2004 |
| JP | 2006-337386 | A | 12/2006 |
| JP | 2007-333706 | A | 12/2007 |
| JP | 2009-145091 | A | 7/2009 |
| JP | 2011-007719 | A | 1/2011 |
| JP | 2011-122823 | A | 6/2011 |
| JP | 05-214420 | A | 6/2013 |
| JP | 2013-0213841 | A | 10/2013 |
| JP | 2015-125018 | A | 7/2015 |

OTHER PUBLICATIONS

Extended European Search Report dated Feb. 6, 2020 for the European Patent Application No. 17833890.1.
Chinese Office Action dated Jun. 2, 2020 for the Chinese Patent Application No. 201780040517.5.

* cited by examiner

[FIG. 1]
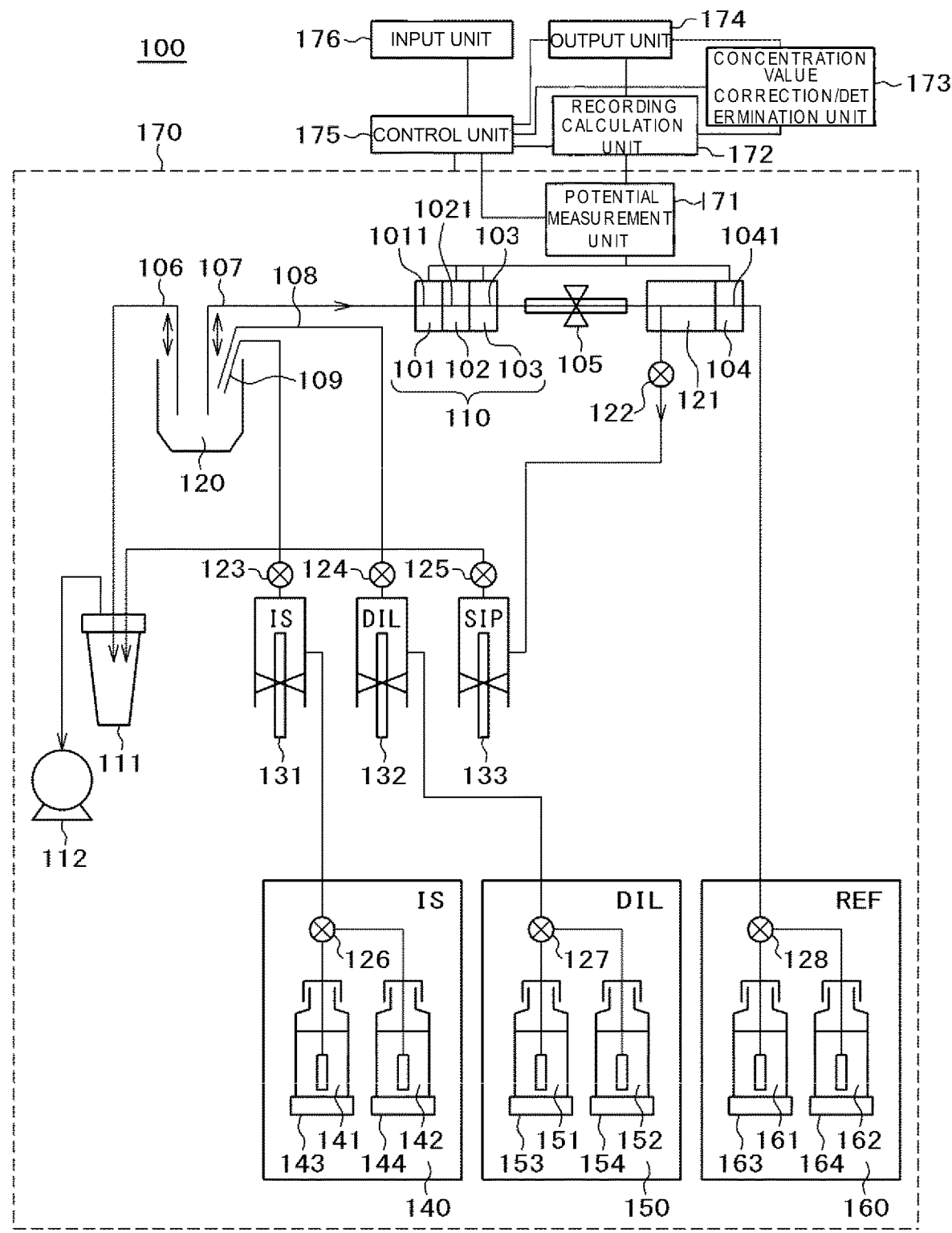

[FIG. 2A]
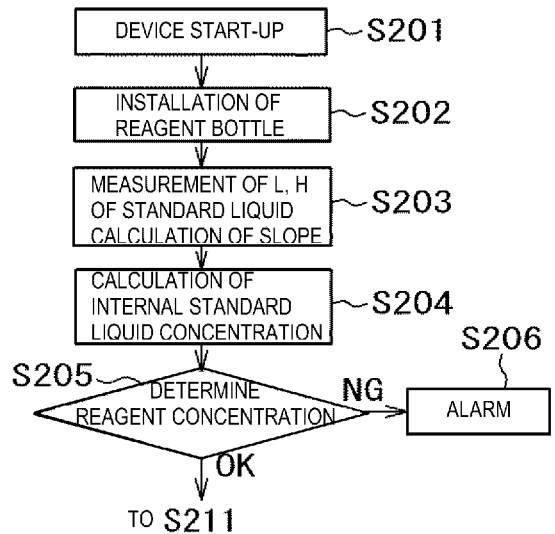
[FIG. 2B]
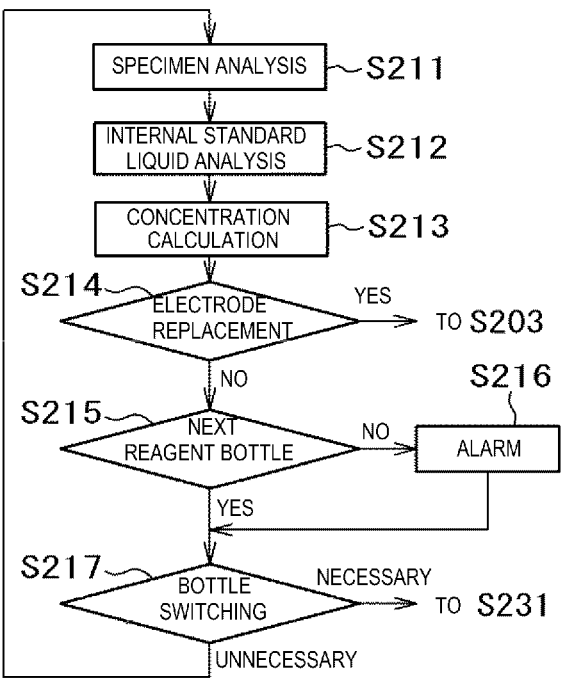

[FIG. 2C]
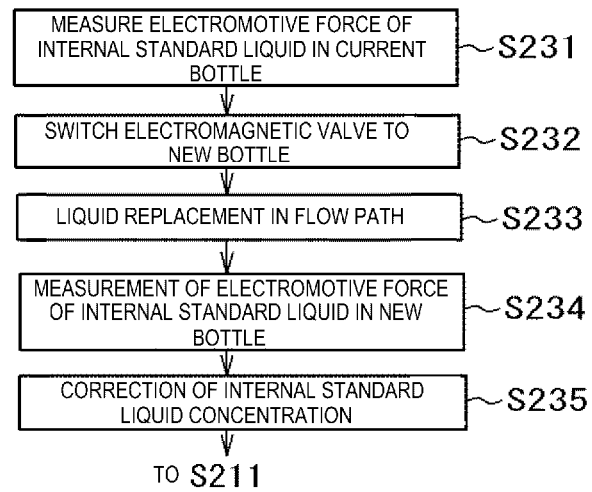

[FIG. 3A]
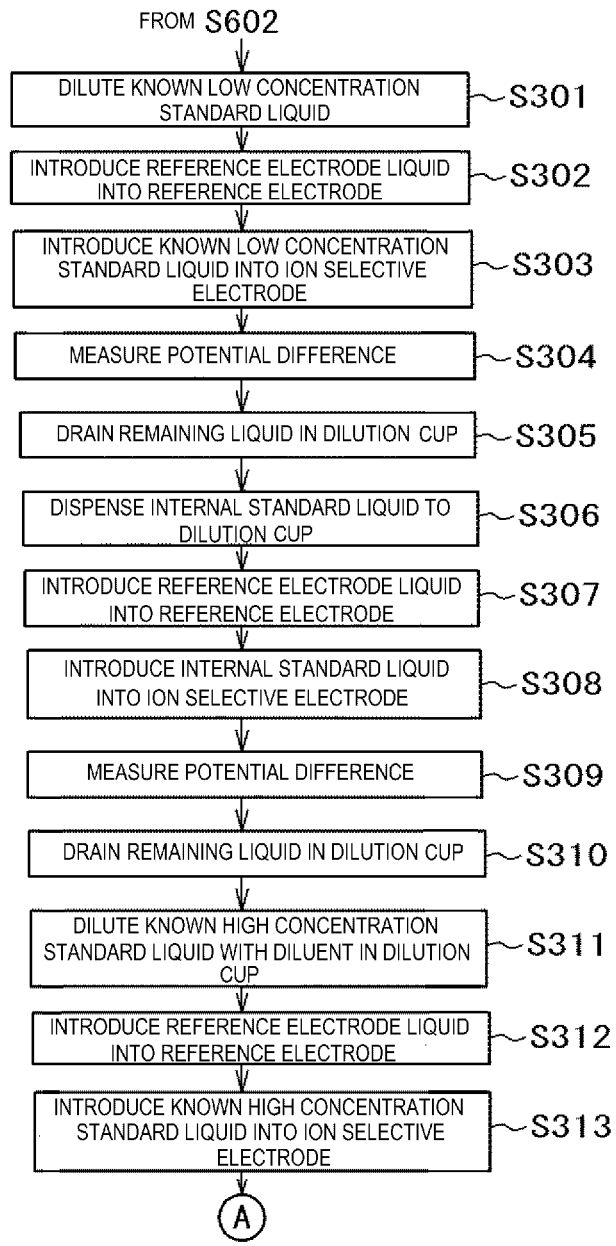

[FIG. 3B]
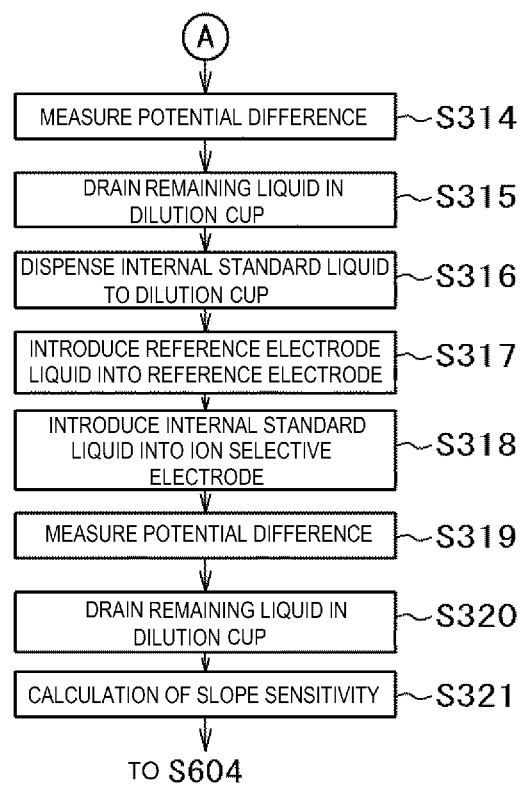

[FIG. 4]
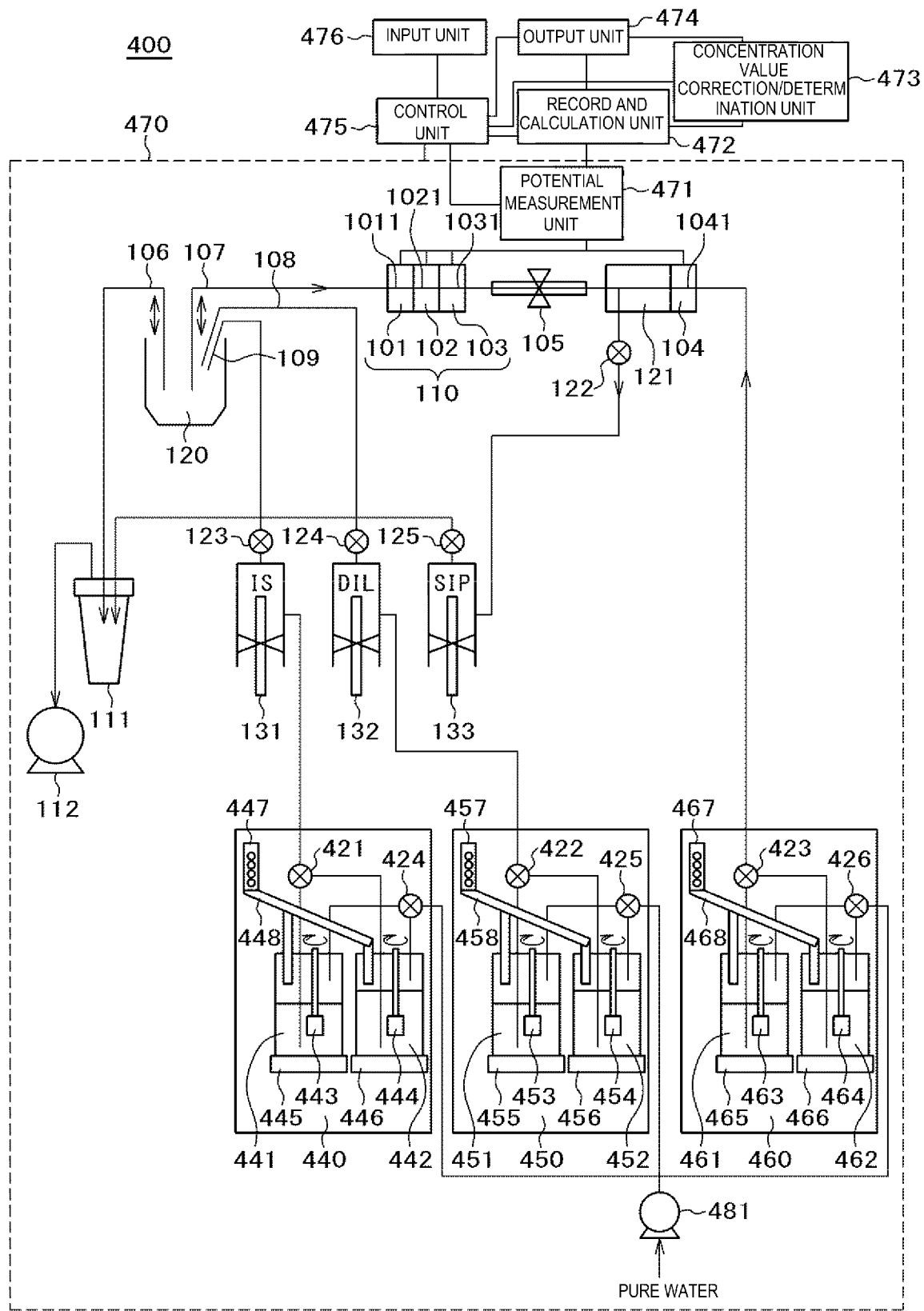

[FIG. 5A]
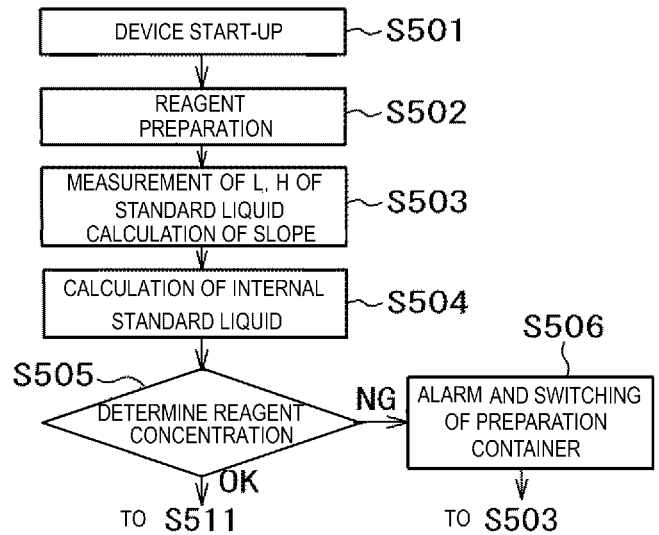
[FIG. 5B]
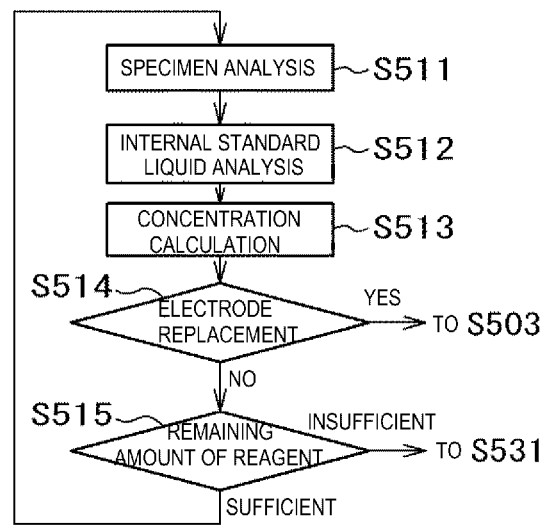

[FIG. 5C]
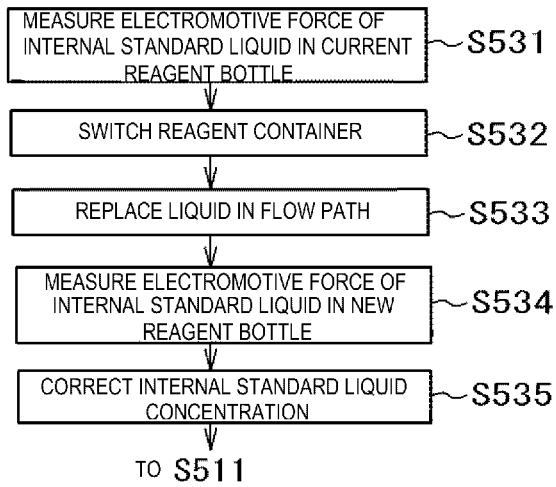
[FIG. 6]
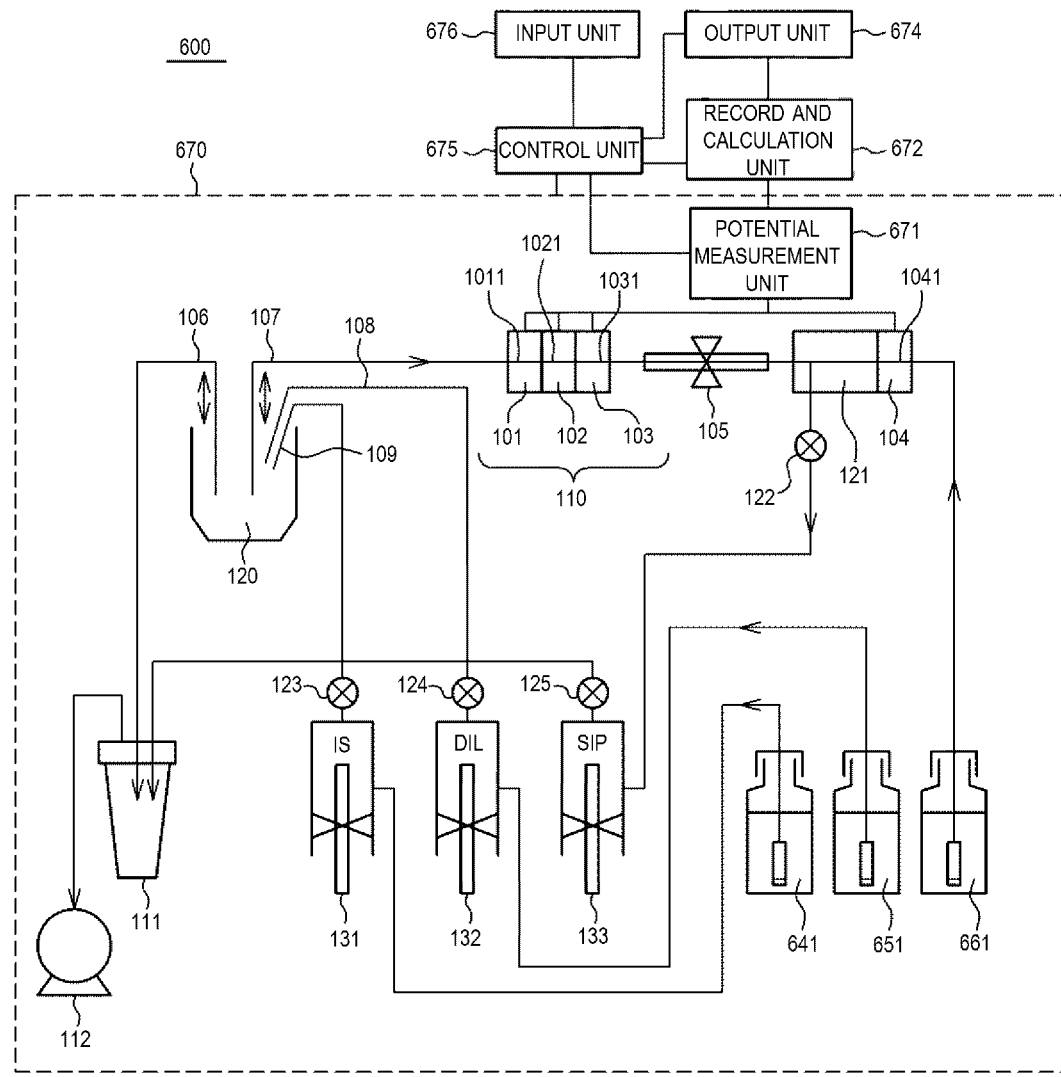

[FIG. 7A]
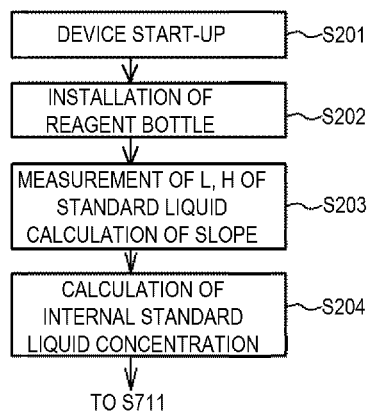
[FIG. 7B]
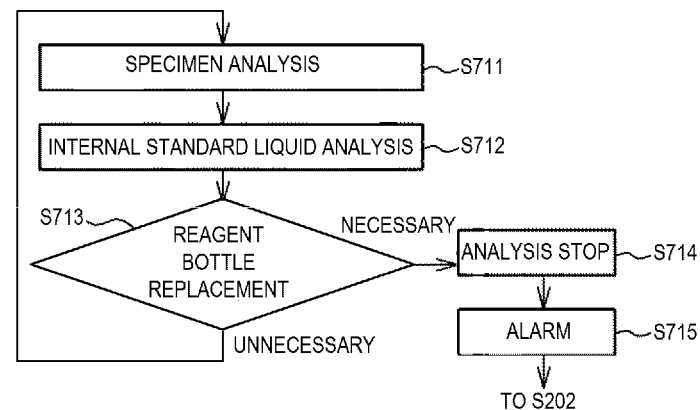

[FIG. 8]
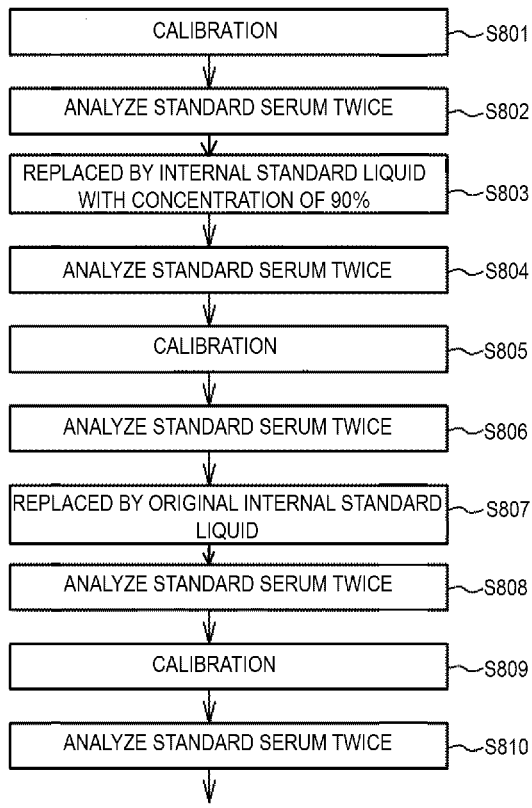
[FIG. 9]
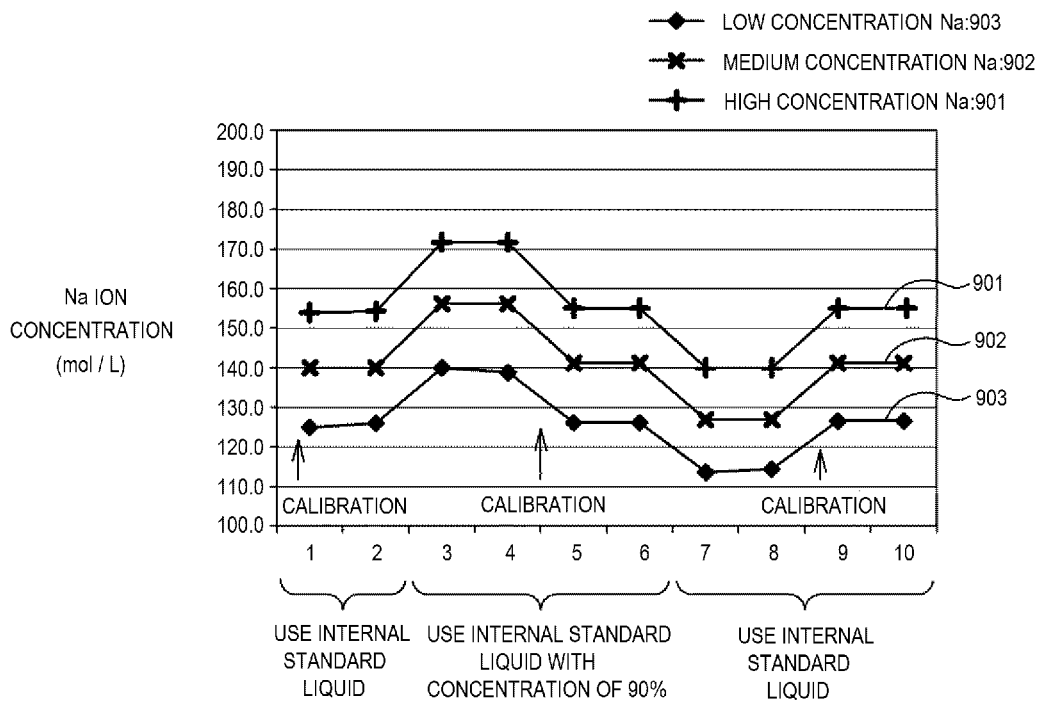

[FIG. 10]
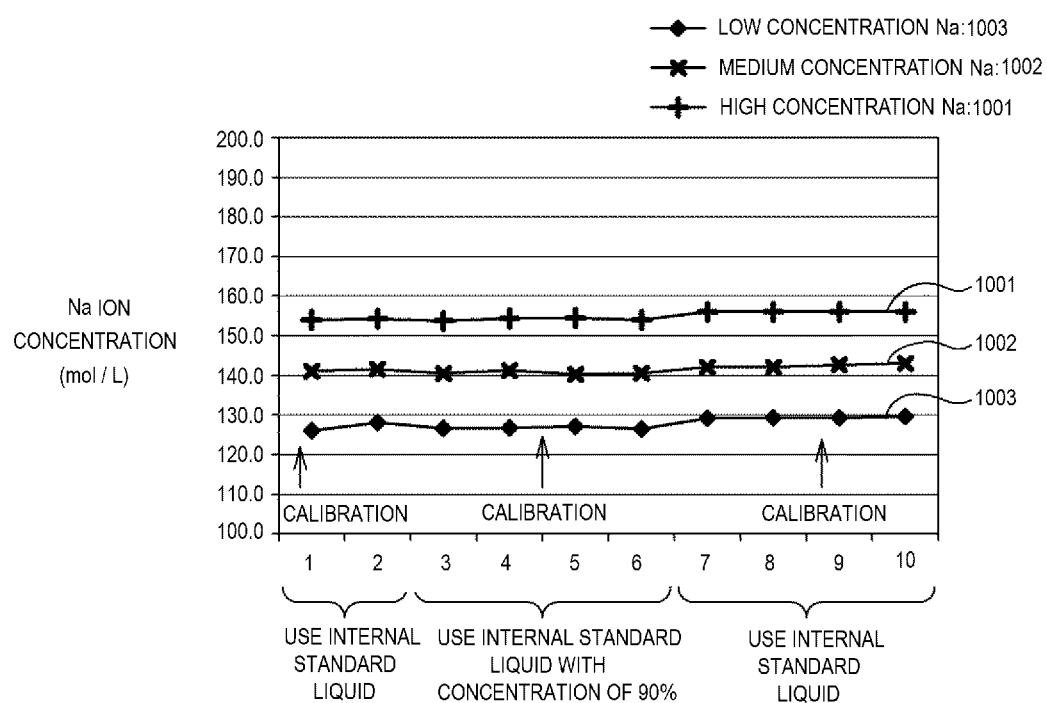

[FIG. 11]
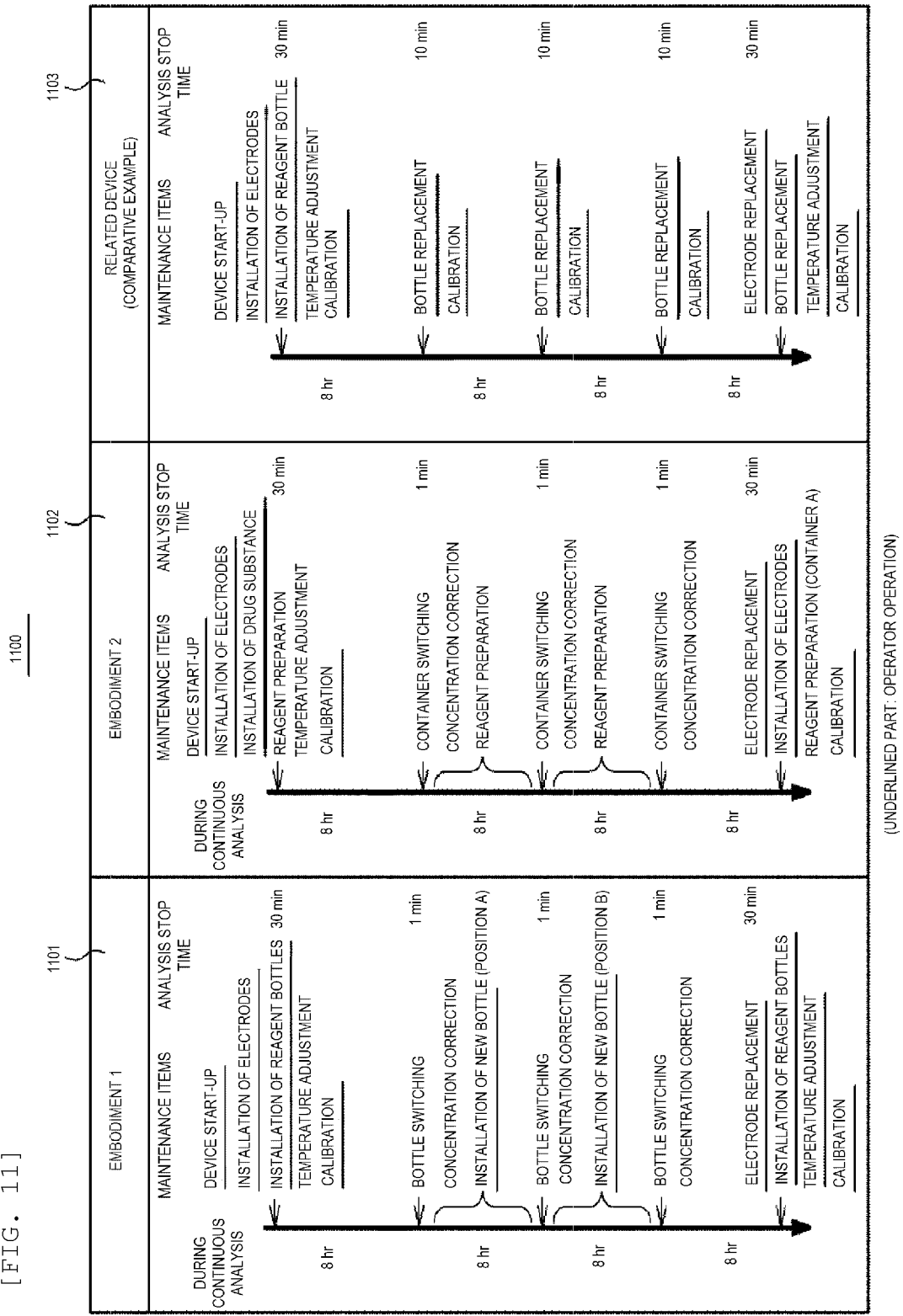

ELECTROLYTE CONCENTRATION MEASUREMENT DEVICE

TECHNICAL FIELD

The present invention relates to an electrolyte concentration measurement device that measures an electrolyte concentration in a liquid.

BACKGROUND ART

An ion to be measured in a sample can be quantified by bringing an ion selective electrode (ISE) into contact with a sample liquid in a detection unit and measuring a potential difference between the ISE and a reference electrode. Due to the simplicity, the ISE is widely used in the field of analysis. Particularly, a flow ion selective electrode is provided with a detection unit in a flow path through which the sample liquid flows, and ion concentrations of a plurality of samples can be qualified continuously.

Therefore, a flow electrolyte concentration measurement device mounted with the flow ion selective electrode is mounted on a biochemical automatic analysis device or the like in which an electrolyte concentration of a specimen such as serum or urine is analyzed with high accuracy and high throughput.

The flow electrolyte concentration measurement device is mounted with a plurality of ion selective electrodes (ISE) corresponding to ions to be detected in order to simultaneously analyze a plurality of ions (sodium ions, potassium ions, calcium ions, chloride ions or the like) in general. Generally, these electrodes are consumables, for example, they are replaced with new electrodes when reaching a service life of two or three months or thousands of tests.

In addition, several types of reagents are constantly used in the electrolyte concentration measurement device to ensure accuracy of analytical values. Although the types of reagents to be used vary depending on a device configuration, the reagents include, for example, an internal standard liquid flowing before and after a specimen analysis, a diluent diluting the specimen, a reference electrode liquid or the like.

When the device is started up or electrodes thereof are replaced, the electrolyte concentration measurement device performs calibration using a standard liquid with a known concentration and creates a calibration curve. In addition, the calibration is also implemented when a reagent bottle is replaced or replenished.

Patent Literature 1 describes a management system that confirms reagent degradation due to a replenishment of the reagent, and an input error of a standard liquid concentration value, and gives a warning.

In addition, Patent Literature 2 describes a reagent adjustment device that adjusts a reagent having a concentration with high accuracy.

PRIOR ART LITERATURE

Patent Literature

PTL 1: JP-A-2013-213841
PTL 2: JP-A-H9-33538

SUMMARY OF INVENTION

Technical Problem

In a related electrolyte concentration measurement device, reagents such as an internal standard liquid and a diluent used in the device are supplied by, for example, a 2 L bottle. In the related device, the bottle is required to be replaced every few hours when the device is operated continuously. In a large scale examination center, a large number of devices are used side by side, and a device operator is bound by a time schedule of reagent bottle replacement.

In addition, the internal standard liquid particularly flows at the interval of two analyses, and a small concentration variation thereof affects an analytical value since the internal standard liquid is a reagent as an analytical standard. Therefore, it is required to re-calibrate the reagent, even when bottles with the same reagent are replaced. During the reagent bottle replacement and calibration, downtime of the device is incurred, which causes a substantial decrease in analytical throughput. In addition, since the reagent is heavy, the transportation cost was burdensome.

Therefore, the invention solves the problems of the above-mentioned related art and provides an electrolyte concentration measurement device simplifying reagent replenishment.

Solution to Problem

In order to solve the above-mentioned problems, the electrolyte concentration measurement device in the invention includes: a measurement unit that includes an ion selective electrode, a reference electrode, and a potential measurement unit, the measurement unit measuring, by the potential measurement unit, a potential difference when an internal standard liquid or specimen is supplied to the ion selective electrode; a reagent supply unit that supplies a reagent containing the internal standard liquid to the measurement unit; a record and calculation unit that processes information on the potential difference measured by the measurement unit and obtains an ion concentration of the internal standard liquid or the specimen; a concentration value correction/determination unit that determines whether the ion concentration of the internal standard liquid, which is obtained by the record and calculation unit, is within a preset value range, and corrects the ion concentration value of the internal standard liquid obtained by the record and calculation unit; an output unit that outputs a result determined by the concentration value correction/determination unit; and a control unit that controls the measurement unit, the record and calculation unit, the concentration value correction/determination unit, and the output unit, in which the reagent supply unit includes a bottle storage unit that stores a plurality of bottles, each accommodating a reagent such as the internal standard liquid, for each type of reagent, and a bottle switching unit that detects a remaining amount of the reagent in each of the plurality of bottles stored in the bottle storage unit, switches a bottle in which the remaining amount of the reagent is smaller than a preset amount due to supplying the reagent to the measurement unit, to a bottle in which the remaining amount of the reagent is sufficiently larger than the preset amount, by a bottle that is stored in the bottle storage unit and accommodates the same type of reagent, and supplies the reagent to the measurement unit, and the concentration value correction/determination unit corrects the ion concentration of the internal standard liquid or the specimen obtained by the record and calculation unit after the bottle accommodating the same type of reagent is switched, by using information of the ion concentration of the internal standard liquid or the specimen obtained by the record and calculation unit before the bottle is switched, when a bottle supplying a reagent to the measurement unit is switched among a plurality of bottles accommodating the same type of reagent in the reagent supply unit.

Advantageous Effect

According to the invention, in a flow electrolyte concentration measurement device, a plurality of bottles with the same type of reagent can be installed in the device and the reagent bottles are automatically switched, so that the device operator can replace the reagent bottles at relatively free timing. In addition, a function of preparing the reagent automatically in the device is added, so that there is no need to replenish the reagent in a longer period of time. As a result, the burden of the operator and downtime of the device can be reduced.

Problems, configurations and effects other than those described above will be apparent with reference to the description of following embodiments.

BRIEF DESCRIPTION OF DRAWINGS

FIG. 1 is a block diagram showing an entire configuration of a flow electrolyte concentration measurement device according to Embodiment 1 of the invention.

FIG. 2A is a flowchart during a device start-up of electrolyte concentration measurement in Embodiment 1 of the invention.

FIG. 2B is a flowchart during a continuous analysis of the electrolyte concentration measurement in Embodiment 1 of the invention.

FIG. 2C is a flowchart during a reagent bottle switching of the electrolyte concentration measurement in Embodiment 1 of the invention.

FIG. 3A is a flowchart from S301 to S313 showing details of S203 of the flow during the device start-up described in FIG. 2A in Embodiment 1 of the invention.

FIG. 3B is a flowchart from S314 to S321 showing details of S203 of the flow during the device start-up described in FIG. 2A in Embodiment 1 of the invention.

FIG. 4 is a block diagram showing an entire configuration of a flow electrolyte concentration measurement device according to Embodiment 2 of the invention.

FIG. 5A is a flowchart during a device start-up of electrolyte concentration measurement in Embodiment 2 of the invention.

FIG. 5B is a flowchart during a continuous analysis of the electrolyte concentration measurement in Embodiment 2 of the invention.

FIG. 5C is a flowchart of a reagent container switching during the device start-up of the electrolyte concentration measurement in Embodiment 2 of the invention.

FIG. 6 is a block diagram showing an entire configuration of a related flow electrolyte concentration measurement device in a comparative example of the invention.

FIG. 7A is a flowchart during a device start-up of electrolyte concentration measurement in the comparative example of the invention.

FIG. 7B is a flowchart of a continuous analysis during the electrolyte concentration measurement in the comparative example of the invention.

FIG. 8 is an experimental flow for demonstrating a stability of an analytical value of the flow electrolyte concentration measurement device in Embodiment 1 of the invention.

FIG. 9 is a graph showing results of a demonstration experiment of a stability of an analytical value in a comparative example device in the comparative example of the invention.

FIG. 10 is a graph showing results of a demonstration experiment of a stability of an analytical value in the flow electrolyte concentration measurement device in Embodiment 1 of the invention.

FIG. 11 is a table showing a comparison between effects of the flow electrolyte concentration measurement devices in Embodiment 1 and Embodiment 2 of the invention and effects of the related device.

DESCRIPTION OF EMBODIMENTS

The inventors conducted research and development in order to devise a method that reduces the burden of a device operator related to a reagent supply during continuous operation while maintaining related high measurement accuracy in a flow electrolyte concentration measurement device. As a result, with respect to an internal standard liquid in a reagent bottle which is considered to be difficult to be replaced without calibration since even a small variation in concentration affects an analytical value, but in the device of the invention, the reagent bottle can be automatically switched without the calibration since an appropriate correction is performed.

In all the drawings for describing this embodiment, the same reference numerals are attached to those having the same function, and the repetitive description thereof will be omitted in principle. Hereinafter, the embodiments of the invention will be described with reference to the drawings.

However, the invention should not be construed as being limited to the following descriptions of the embodiments. Those skilled in the art can easily understand that specific configurations can be changed without departing from the spirit or gist of the invention.

First Embodiment

FIG. 1 is a schematic block diagram showing an example of a flow electrolyte concentration measurement device 100 according to the embodiment. The flow electrolyte concentration measurement device 100 includes a measurement unit 170, a record and calculation unit 172, a concentration value correction/determination unit 173, an output unit 174, a control unit 175, and an input unit 176.

The measurement unit 170 includes three types of electrodes including a chloride ion electrode 101, a potassium ion electrode 102, and a sodium ion electrode 103 which configure an ion selective electrode unit 110, and a reference electrode 104. A reference electrode liquid is introduced from a reference electrode liquid bottle 161 or 162 to a flow path 1041 of the reference electrode 104 by using a sipper syringe pump 133.

Meanwhile, an internal standard liquid dispensed from an internal standard liquid bottle A: 141 or B: 142, or a diluted specimen in a dilution cup 120 is introduced into flow paths 1011, 1021 and 1031 of the ion selective electrode unit 110. Since Potential differences (electromotive force) between the ion selective electrodes 101, 102 and 103 and the reference electrode 104 vary according to a concentration of an ion to be analyzed in a liquid that is introduced into the flow paths 1011, 1021 and 1031 of the ion selective electrodes 101, 102 and 103, the electromotive force is measured by a potential measurement unit 171, and the ion concentration is calculated by the record and calculation unit 172. Details of the calculation method will be described below.

Since the reference electrode liquid, the internal standard liquid, and a diluent are constantly used in the flow electrolyte concentration measurement device 100 according to this embodiment, an analysis cannot be performed if any of reagents is insufficient during a continuous analysis.

The flow electrolyte concentration measurement device 100 according to this embodiment includes an internal standard liquid reagent bottle switching unit 140, a diluent bottle switching unit 150, and a reference electrode liquid bottle switching unit 160. These bottle switching units include ports simultaneously installed with two bottles 141 and 142, 151 and 152, 161 and 162 with the same type of reagent, and switching valves including electromagnetic valves 126, 127 and 128 respectively. By means of this mechanism, when a reagent in one bottle is insufficient, it is possible to switch to the other bottle. In addition, when the device uses one bottle, a device operator can replace an empty bottle with a new bottle filled with a reagent at a desired timing.

The flow electrolyte concentration measurement device 100 according to this embodiment includes reagent amount monitoring mechanisms (weight sensors 143, 144, 153, 154, 163 and 164 each measuring the weight of a reagent bottle in the example shown in FIG. 1) that monitor the amount of the reagents in each of the reagent bottles 141, 142, 151, 152, 161, and 162, and manages a timing of reagent bottle switching by comparing the weight of the reagent bottle with a preset value, and switching to a bottle where the reagent is sufficiently accommodated when the weight of a reagent bottle is lighter than the preset weight. It is not limited to using the weight sensor as the reagent amount monitoring mechanism, and a liquid level meter that monitors the height of a liquid level of a reagent liquid in the reagent bottle or the like may be used as a reagent amount monitoring mechanism. In addition, even if the reagent amount monitoring mechanism is not provided, the control unit 175 may manage a reagent consumption amount from an analysis frequency, a syringe operation history, or the like.

Electromagnetic valves 122, 123, 124, 125, 126, 127, and 128 can switch or open/close flow paths, and operates appropriately according to a direction and a timing of introducing a liquid. In addition, although two bottles with the same type of reagent are installed in the flow electrolyte concentration measurement device 100 according to this embodiment, the effect of the invention will be exerted as long as the number of the bottles with the same type of reagent is plural, even if it is not two. The invention can also be applied to only some of the reagents instead of all types of reagents used in the device.

Next, a flow of electrolyte concentration measurement in the flow electrolyte concentration measurement device 100 according to this embodiment will be described with reference to FIGS. 2A to 2C.

First, a procedure during a device start-up will be described with reference to FIG. 2A. First, a power source (not shown) is turned on to start up the device (S201), and the reagent bottle 141 (internal standard liquid bottle A 141) and the reagent bottle 142 (internal standard liquid bottle B 142), the reagent bottle 151 (diluent bottle A 151) and the reagent bottle 152 (diluent bottle B 152), and the reagent bottle 161 (reference electrode liquid bottle A 161) and the reagent bottle 162 (reference electrode liquid bottle B 162) are respectively installed in the bottle switching units 140, 150 and 160 (S202). After the temperature adjustment, in order to obtain calibration curves of the ion selective electrodes 101, 102 and 103, two types of standard liquids with known concentrations are measured, and a slope is calculated (S203). Subsequently, an internal standard liquid concentration is calculated (S204).

Here, specific operations of S203 and S204 will be described with reference to the flowchart of FIG. 3.

First, after a known low concentration standard liquid is dispensed into the dilution cup 120 by a dispensing nozzle (not shown), a diluent in the diluent bottle 151 (bottle 151) is dispensed into the dilution cup 120 by operating a diluent syringe pump 132, and the known low concentration standard liquid is diluted in a set ratio D (S301). In the meantime, the reference electrode liquid is introduced into the flow path 1041 of the reference electrode 104 from the reference electrode liquid bottle 161 (S302). Next, the diluted known low concentration standard liquid in the dilution cup is sucked from a sipper nozzle 107, and introduced into the flow paths 1011, 1021 and 1031 of the ion selective electrodes 101, 102 and 103 (S303).

In a liquid junction unit 121, the reference electrode liquid supplied to the flow path 1041 of the reference electrode 104 is brought into contact with the diluted known low concentration standard liquids supplied to the flow paths 1011, 1021 and 1031 of the ion selective electrodes 101, 102 and 103. In this state, each potential difference (electromotive force) between each of the ion selective electrodes 101, 102, and 103 and the reference electrode 104 is measured by the potential measurement unit 171 (S304).

Next, a vacuum pump 112 is driven, and the remaining liquid in the dilution cup 120 is sucked up by a vacuum suction nozzle 106 and drained in a waste liquid tank 111 (S305). Thereafter, an internal standard liquid syringe pump 131 is operated so as to dispense the internal standard liquid in the internal standard liquid bottle 141 (bottle 141) from an internal standard liquid supply nozzle 109 to the dilution cup 120 (S306). In the meantime, when a pinch valve 105 is closed and the electromagnetic valve 122 is opened, the sipper syringe pump 133 is operated so as to introduce the reference electrode liquid into the flow path 1041 of the reference electrode 104 from the reference electrode liquid bottle 161 (S307).

Next, when the pinch valve 105 is opened and the electromagnetic valve 128 is closed, the internal standard liquid in the dilution cup 120 is sucked from the sipper nozzle 107, and the flow paths 1011, 1021, and 1031 of the ion selective electrodes 101, 102 and 103 are filled with the internal standard liquid (S308). In this state, each potential difference (electromotive force) between each of the ion selective electrodes 101, 102, and 103 and the reference electrode 104 is measured by the potential measurement unit 171 (S309).

Thereafter, the vacuum pump 112 is further driven, the remaining liquid in the dilution cup 120 is sucked up by the vacuum suction nozzle 106 and drained in the waste liquid tank 111 (S310). Thereafter, after a known high concentration standard liquid is dispensed into the dilution cup 120 by a dispensing nozzle (not shown), a diluent in the diluent bottle 151 is dispensed into the dilution cup 120 from a diluent supply nozzle 108 by operating the diluent syringe pump 132, and the known high concentration standard liquid is diluted in the set ratio D (S311). In the meantime, when the pinch valve 105 is closed and the electromagnetic valve 122 is open, the sipper syringe pump 133 is operated so as to introduce the reference electrode liquid into the flow path 1041 of the reference electrode 104 from the reference electrode liquid bottle 161 (S312).

Next, when the pinch valve 105 is open and the electromagnetic valve 128 is closed, the diluted known high concentration standard liquid in the dilution cup 120 is sucked from the sipper nozzle 107 and introduced into the flow paths 1011, 1021 and 1031 of the ion selective electrodes 101, 102 and 103 (S313). In the liquid junction unit 121, the reference electrode liquid supplied to the flow path 1041 of the reference electrode 104 is brought into contact with the diluted known high concentration standard liquids supplied to the flow paths 1011, 1021 and 1031 of the ion selective electrodes 101, 102 and 103. In this state, each potential difference (electromotive force) between each of the ion selective electrodes 101, 102, and 103 and the reference electrode 104 is measured by the potential measurement unit 171 (S314).

Next, the vacuum pump 112 is driven, and the remaining liquid in the dilution cup 120 is sucked up by the vacuum suction nozzle 106 and drained in the waste liquid tank 111 (S315). Thereafter, the internal standard liquid syringe pump 131 is operated so as to dispense the internal standard liquid in the internal standard liquid bottle 141 from the internal standard liquid supply nozzle 109 to the dilution cup 120 (S316). In the meantime, when the pinch valve 105 is closed and the electromagnetic valve 122 is opened, the sipper syringe pump 133 is operated so as to introduce the reference electrode liquid into the flow path 1041 of the reference electrode 104 from the reference electrode liquid bottle 161 (S317).

Next, when the pinch valve 105 is open and the electromagnetic valve 128 is closed, the internal standard liquid in the dilution cup 120 is sucked from the sipper nozzle 107, and the flow paths 1011, 1021, and 1031 of the ion selective electrodes 101, 102 and 103 are filled with the internal standard liquid respectively (S318), and in this state, each potential difference (electromotive force) between each of the ion selective electrodes 101, 102, and 103 and the reference electrode 104 is measured by the potential measurement unit 171 (S319).

Thereafter, the vacuum pump 112 is further driven, the remaining liquid in the dilution cup 120 is sucked up by the vacuum suction nozzle 106 and drained in the waste liquid tank 111 (S320).

A slope sensitivity (SL) corresponding to the calibration curve is calculated by the record and calculation unit 172 from the electromotive force measured by the potential measurement unit 171 through the above operations by using the following calculation formulas (S321).

(A) Slope Sensitivity $$SL = (EMFH - EMFL)/(\log CH - \log CL) \quad \text{(Formula 1)}$$

SL: slope sensitivity
EMFH: measured electromotive force of known high concentration standard liquid
EMFL: measured electromotive force of known low concentration standard liquid
CH: known concentration value of high concentration standard liquid
CL: known concentration value of low concentration standard liquid The above operation is called calibration. Incidentally, the slope sensitivity (SL) corresponds to $2.303 \times (RT/zF)$ of the Nernst equation $$E = E0 + 2.303 \times (RT/zF) \times \log(f \times C)$$

(E0: constant potential determined by a measurement system; z: valence of an ion to be measured; F: Faraday constant; R: gas constant; T: absolute temperature; f: activity coefficient; C: ion concentration). Although the slope sensitivity can be calculated from the temperature and the valence of the ion to be measured, the slope sensitivity (SL) specific to an electrode is obtained by the above-mentioned calibration in the device of this embodiment in order to further improve the analysis accuracy.

Although the specific measurement sequence with respect to the details of S203 has been mentioned above, regardless of this procedure, a different procedure may be adopted as long as two types of liquids having different ion concentrations are respectively introduced into the flow path and the electromotive force can be measured.

Subsequently, the internal standard liquid concentration is calculated from the slope sensitivity obtained in S203 and the electromotive force of the internal standard liquid (S204).

(B) Internal Standard Liquid Concentration $$CIS = CL \times 10^a \quad \text{(Formula 2)}$$

$$a = (EMFIS - EMFL)/SL \quad \text{(Formula 3)}$$

CIS: concentration of internal standard liquid
EMFIS: electromotive force of internal standard liquid Next, the concentration value correction/determination unit 173 determines whether the ion concentration of the internal standard liquid is within a set concentration range (S205), and the procedure proceeds to a flow of the continuous analysis shown in FIG. 2B if it is within the range, and an alarm is issued if it is out of the range (S206). When the concentration of a reagent used in the device significantly differs from a design value, the analysis accuracy may be affected in consideration of the irregular device state, so that the present device includes the concentration value correction/determination unit 173.

Next, the operations during the continuous analysis will be described with reference to the flowchart shown in FIG. 2B. After the calibration, serum, urine, or the like are analyzed as the specimen. Although in the processing flow shown in FIG. 2B, there is a detailed operation which is described as the way in which the step of S203 of FIG. 2A is described by the flowchart shown in FIGS. 3A and 3B, in order to simplify the description, the description of a detailed operation is omitted.

Specifically, after the specimen is dispensed into the dilution cup 120 by the dispensing nozzle (not shown), the diluent in the diluent bottle 151 is dispensed into the dilution cup 120 by using the diluent syringe pump 132 and the specimen is diluted in the set ratio D. In the meantime, the reference electrode liquid is introduced into the flow path of the reference electrode 104 from the reference electrode liquid bottle 161. The diluted specimen in the dilution cup 120 is sucked from the sipper nozzle 107 and introduced into the flow paths 1011, 1021 and 1031 of the ion selective electrodes 101, 102 and 103.

In the liquid junction unit, the reference electrode liquid is brought into contact with the diluted specimen. Each potential difference (electromotive force) between the ion selective electrodes 101, 102 and 103 and the reference electrode 104 is measured by the potential measurement unit 171 (S211). After the remaining liquid in the dilution cup 120 is sucked up by the vacuum suction nozzle 106 and drained into the waste liquid tank 111 by operating the vacuum pump 112, the internal standard liquid in the internal standard liquid bottle 141 is dispensed into the dilution cup 120. In the meantime, when the pinch valve 105 is closed and the electromagnetic valve 122 is opened, the sipper syringe pump 133 is operated so as to drain the liquid remaining in the flow path 1041 of the reference electrode 104 into the waste liquid tank 111 and introduce the reference electrode liquid into the flow path 1041 of the reference electrode 104 from the reference electrode liquid bottle 161.

Next, the internal standard liquid in the dilution cup 120 is sucked from the sipper nozzle 107, and the electromotive force of each electrode is measured by the potential measurement unit 171 in a state where the flow paths 1011, 1021 and 1031 of the ion selective electrodes 101, 102 and 103 are filled up with the internal standard liquid (S212). Thereafter, the remaining liquid in the dilution cup 120 is sucked up by the vacuum suction nozzle 106 and drained into the waste liquid tank 111.

The concentration of the specimen is calculated from the slope sensitivity obtained in S203 and the internal standard liquid concentration calculated in S204 by using the following calculation formulas (S213).

(C) Concentration of the Specimen $$CS = CIS \times 10^b \qquad \text{(Formula 4)}$$

$$b = (EMFIS - EMFS)/SL \qquad \text{(Formula 5)}$$

CS: Concentration of the specimen
EMFS: Measured electromotive force of the specimen The above calculation formulas are basic, and various corrections such as temperature drift and carryover may be added. Further, during the analysis, a liquid for refreshing may be introduced into the dilution cup or the flow paths.

During the analysis, if a user replaces any one of the ion selective electrodes 101, 102 and 103 or the reference electrode 104, the electrode replacement detection mechanism (not shown) detects that the electrode is replaced (S214) and the calibration operation will be performed. If the electrode is not replaced, the reagent bottle replacement detection mechanism (not shown) detects whether the reagent bottle to be switched next is installed (S215), and if not installed, an alarm is issued (S216). If the alarm is issued, the device operator takes out the empty bottle and installs a new reagent bottle before the next reagent bottle switching.

Next, it is determined whether it is necessary to switch the reagent bottle (S217). If unnecessary, the specimen is continuously analyzed, and if necessary, the reagent bottle switching shown in the flowchart of FIG. 2C is performed.

Here, the operation at the time of switching the reagent bottle will be described based on the flowchart of FIG. 2C. Although there is a detailed operation which is described as the way in which the step of S203 of FIG. 2A is described by the flowchart of FIGS. 3A and 3B in the processing flow shown in FIG. 2C, in order to simplify the description, the description of detailed operation is omitted.

First, before switching the reagent bottle, the internal standard liquid in the currently used reagent bottle, for example, the internal standard liquid bottle A141 (bottle 141), is dispensed into the dilution cup 120. In the meantime, the reference electrode liquid is introduced into the flow path 1041 of the reference electrode 104 from the reference electrode liquid bottle A161. The potential differences (electromotive forces) between each ion selective electrode 101, 102 and 103 and the reference electrode 104 are measured by the potential measurement unit 171 in a state where the internal standard liquid in the dilution cup 120 is sucked from the sipper nozzle 107 and the flow paths 1011, 1021 and 1031 of the ion selective electrodes 101, 102 and 103 are filled up with the internal standard liquid (S231).

Next, the remaining liquid in the dilution cup is sucked up by the vacuum suction nozzle 106 and drained into the waste liquid tank 111 by operating the vacuum pump 112. Next, the reagent is supplied from the new bottle by switching the electromagnetic valve (S232), and the liquid in the supply flow path is replaced (S233). Thereafter, the internal standard liquid in the internal standard liquid bottle B142 is dispensed into the dilution cup. In the meantime, the reference electrode liquid is introduced into the flow path of the reference electrode 104 from the reference electrode liquid bottle B162.

Next, the potential differences (electromotive forces) between each ion selective electrode 101, 102 and 103 and the reference electrode 104 are measured by the potential measurement unit 171 in a state where the internal standard liquid in the dilution cup is sucked from the sipper nozzle 107 and the flow paths 1011, 1021 and 1031 of the ion selective electrodes 101, 102 and 103 are filled up with the internal standard liquid (S234). The remaining liquid in the dilution cup 120 is sucked up by the vacuum suction nozzle 106 and drained into the waste liquid tank 111.

Next, the concentration value of the internal standard liquid is calculated by the following formulas, and the concentration value correction/determination unit 173 determines whether the concentration is not abnormal and corrects the concentration value of the internal standard liquid (S235). The slope sensitivity (SL) is the value calculated by Formula 1.

(D) Internal Standard Liquid Concentration Correction $$CIS' = CIS \times 10^c \qquad \text{(Formula 6)}$$

$$c = (EMFIS' - EMFIS)/SL \qquad \text{(Formula 7)}$$

CIS: Concentration of the internal standard liquid in the currently used bottle
CIS': Concentration of the internal standard liquid in the new bottle
EMFIS: Electromotive force of the internal standard liquid in the currently used bottle
EMFIS': Electromotive force of the internal standard liquid in the new bottle Then, the continuous analysis is automatically restarted.

In this concentration correction, since the reagent after switching is measured by the ion selective electrode itself used for the analysis of the specimen, an accurate correction can be performed.

Regarding the above-mentioned concentration correction, the value can also be calculated from the value of the slope sensitivity at the time of calibration and the value of the electromotive force when the standard liquid of known concentration is measured. The reagents may be switched one by one instead of three types at the same time.

According to this embodiment, since the reagent concentration measurement and the correction are appropriately performed at the timing of the reagent container switching, even if there are some concentration adjustment errors at the time of switching, the analytical value will not be shifted. Accordingly, in the flow electrolyte concentration measurement device according to this embodiment, since some concentration errors occurring between the reagent bottles can be absorbed, the reagent bottle can be automatically switched, and the operator's load and device downtime can be reduced.

Embodiment 2

A flow electrolyte concentration measurement device 400 according to a second embodiment of the invention will be described with reference to FIG. 4. The flow electrolyte concentration measurement device 400 according to this embodiment includes an internal standard liquid preparation unit 440, a diluent preparation unit 450, a reference electrode liquid preparation unit 460 in place of the reagent bottle switching units 140, 150 and 160 described in Embodiment 1, and a measurement unit 470. Components having the same configuration as those in Embodiment 1 are denoted by the same numbers.

The internal standard liquid preparation unit 440 is provided with an internal standard liquid preparation container A441, an internal standard liquid preparation container B442, and a drug substance supply unit 448 that supplies a drug substance 447. In addition, a pure water supply pump 481 that introduces pure water into each preparation container, stirring mechanisms 443 and 444 that stir and mix the drug substance 447 and the pure water, and switching valves (electromagnetic valves 421, 422 and 423) for the preparation containers A and the preparation containers B are provided. The diluent preparation unit 450 and the reference electrode liquid preparation unit 460 respectively include a diluted drug substance supply unit 458 that supplies the diluted drug substance 457 and a reference electrode drug substance supply unit 468 that supplies the reference electrode liquid substance 467 which are similar.

The flow electrolyte concentration measurement device 400 according to this embodiment can automatically prepare a reference electrode liquid, an internal standard liquid, and a diluent, which are reagents constantly used in the device, during a continuous analysis. For example, while continuous analysis is performed using the reagent in the internal standard liquid preparation container A441, a new reagent can be prepared in the other internal standard liquid preparation container B442 and when the reagent in the internal standard liquid preparation container A441 is insufficient, the switching to the internal standard liquid preparation container B442 can be automatically performed, the concentration correction can be automatically performed, and the analysis can be continued. It also applies to the diluent preparation unit 450 and the reference electrode liquid preparation unit 460. Accordingly, the reagent replenishment interval can be much longer than that of the conventional device. Therefore, the device operator may replenish the drug substance, for example, at the timing of electrode replacement.

The flow electrolyte concentration measurement device 400 according to this embodiment includes reagent amount monitor mechanisms (weight sensors 445, 446, 455, 456, 465 and 466 that measure the weight of each reagent bottle in the example shown in FIG. 4) that monitor the amount of the reagent in each reagent container, and manages the timing of the reagent container switching by comparing the measured weight of each reagent bottle with a preset value. It is not limited to using the weight sensor as the reagent amount monitor mechanism, and a liquid level meter that monitors the height of the liquid level of the reagent liquid in the reagent bottle or the like may be used. Further, even if the reagent amount monitor mechanism is not provided, the control unit 475 may manage the reagent consumption amount from the analysis frequency, the syringe operation history, or the like. In addition, although two reagent preparation containers of the same type are installed in the flow electrolyte concentration measurement device 400 in this embodiment, the effect of the invention will be exerted as long as the number of the reagent preparation containers with same type is plural, even if it is not two. The invention can also be applied to only some of the reagents instead of all types of the reagents used in the device.

The flow of the electrolyte concentration measurement of the flow electrolyte concentration measurement device 400 in this embodiment will be described with reference to FIGS. 5A to 5C.

First, a procedure at the time of device start-up will be described based on the flow of FIG. 5A. At first, the device is started up (S501), and the reagent preparation is started (S502). At this time, the internal standard liquid, the diluent, and the reference electrode liquid are preferentially prepared in the preparation containers A respectively, and upon completion, the preparations in the preparation containers B are started. In the case of the internal standard liquid, the drug substance 447 is put into the preparation container A441 by using the drug substance supply unit 448. The internal standard liquid is prepared by supplying pure water to the preparation container A441 using the pure water supply pump 481 while stirring by the stirring unit 443. At this time, it is important that the concentration in the container becomes uniform without undissolved residues of the drug substance.

After the temperature adjustment, in order to obtain calibration curves of the ion selective electrodes 101, 102 and 103, two types of standard liquids with known concentrations are measured and a slope is calculated (S503). Subsequently, the prepared internal standard liquid concentration is calculated (S504).

Here, specific operations of S503 and S504 will be described. After the known low concentration standard liquid is dispensed into the dilution cup 120 by the dispensing nozzle (not shown), the diluent in the diluent preparation container A451 is dispensed into the dilution cup by using the diluent syringe pump 132 and the known low concentration standard liquid is diluted in the set ratio D (corresponding to S301 described in the flowchart of FIG. 3 in Embodiment 1. The corresponding relationship with steps in the flowchart of FIG. 3 is shown below). In the meantime, the reference electrode liquid is introduced into the flow path of the reference electrode 104 from the reference electrode liquid container A461 (corresponding to S302).

The diluted known low concentration standard liquid in the dilution cup is sucked from the sipper nozzle and introduced into the flow paths 1011, 1021 and 1031 of the ion selective electrodes 101, 102 and 103 (corresponding to S303). In the liquid junction unit 121, the reference electrode liquid is brought into contact with the diluted known low concentration standard liquid. Each potential difference (electromotive force) between the ion selective electrodes 101, 102 and 103 and the reference electrode 104 is measured by the potential measurement unit 471 (corresponding to S304).

After each potential difference is measured, the remaining liquid in the dilution cup 120 is sucked up by the vacuum suction nozzle 106 and drained into the waste liquid tank 111 (corresponding to S305), the internal standard liquid in the internal standard liquid preparation container A441 is dispensed into the dilution cup 120 (corresponding to S306). In the meantime, the reference electrode liquid is introduced into the flow path 1041 of the reference electrode 104 from the reference electrode liquid preparation container A461 (corresponding to S307).

Next, the internal standard liquid in the dilution cup 120 is sucked from the sipper nozzle 107, and the flow paths of each ion selective electrode 101, 102 and 103 are filled up with the internal standard liquid (corresponding to S308). In this state, each potential difference (electromotive force) between the ion selective electrodes 101, 102 and 103 and the reference electrode 104 is measured by the potential measurement unit 471 (corresponding to S309).

After each potential difference is measured, the remaining liquid in the dilution cup 120 is sucked up by the vacuum suction nozzle 106 and drained into the waste liquid tank 111

(corresponding to S310), and the known high concentration standard liquid is dispensed into the dilution cup 120 by the dispensing nozzle (not shown), and then the diluent in the diluent preparation container A451 is dispensed into the dilution cup 120 by using the diluent syringe pump 132 and the known high concentration standard liquid is diluted in the set ratio D (corresponding to S311). In the meantime, the reference electrode liquid is introduced into the flow path of the reference electrode 104 from the reference electrode liquid preparation container A461 (corresponding to S312).

After the dispensation of the diluent into the dilution cup 120 is completed, the diluted known high concentration standard liquid in the dilution cup 120 is sucked from the sipper nozzle and introduced into the flow paths 1011, 1021 and 1031 of the ion selective electrodes 101, 102 and 103 (corresponding to S313). In the liquid junction unit 121, the reference electrode liquid is brought into contact with the diluted known high concentration standard liquid. Each potential difference (electromotive force) between each ion selective electrode 101, 102 and 103 and the reference electrode 104 is measured by the potential measurement unit 471 (corresponding to S314).

After the measurement of each potential difference is completed, the remaining liquid in the dilution cup is sucked up by the vacuum suction nozzle 106 and drained into the waste liquid tank 111 (corresponding to S315), and then the internal standard liquid in the internal standard liquid preparation container A441 is dispensed into the dilution cup 120 (corresponding to S316). In the meantime, the reference electrode liquid is introduced into the flow path of the reference electrode 104 from the reference electrode liquid preparation container A461 (corresponding to S317).

The internal standard liquid in the dilution cup 120 is sucked from the sipper nozzle 107 and the flow paths of the ion selective electrodes 101, 102 and 103 are filled up with the internal standard liquid (corresponding to S318), and in this state, each potential difference (electromotive force) between each ion selective electrode 101, 102 and 103 and the reference electrode 104 is measured by the potential measurement unit 471 (S319). Further, the remaining liquid in the dilution cup 120 is sucked up by the vacuum suction nozzle 106 and drained into the waste liquid tank 111 (corresponding to S320).

The slope sensitivity (SL) corresponding to the calibration curve is calculated by the record and calculation unit 472 from the electromotive force measured by the potential measurement unit 471 by using the following calculation formula (corresponding to S321).

(A) Slope Sensitivity $$SL=(EMFH-EMFL)/(\text{Log } CH-\text{Log } CL) \quad \text{(Formula 8)}$$

SL: slope sensitivity
EMFH: Measured electromotive force of the known high concentration standard liquid
EMFL: Measured electromotive force of the known low concentration standard liquid
CH: Known concentration of the high concentration standard liquid
CL: Known concentration of the low concentration standard liquid The above operation is called calibration. The slope sensitivity (SL) corresponds to $2.303\times(RT/zF)$ of the Nernst equation $$E=E0+2.303+(RT/zF)\times\log(f\times C)$$

(E0: constant potential determined by measurement system, z: valence of ion to be measured, F: Faraday constant, R: gas constant, T: absolute temperature, f: activity coefficient, C: ion concentration). Although the slope sensitivity can be calculated from the temperature and the valence of ion to be measured, the slope sensitivity (SL) specific to an electrode is obtained by the above-mentioned calibration in the device of this embodiment in order to further improve the analysis accuracy.

Although the specific measurement sequence with respect to the details of S503 has been mentioned above, regardless of this procedure, a different procedure may be adopted as long as two types of liquids having different ion concentrations are respectively introduced into the flow paths and the electromotive force can be measured.

Subsequently, the internal standard liquid concentration is calculated from the slope sensitivity obtained in S503 and the electromotive force of the internal standard liquid (S504).

(B) Concentration of Internal Standard Liquid $$CIS=CL\times 10^{a} \quad \text{(Formula 9)}$$

$$a=(EMFIS-EMFL)/SL \quad \text{(Formula 10)}$$

CIS: Concentration of internal standard liquid
EMFIS: Electromotive force of the internal standard liquid Next, the concentration value correction/determination unit 473 determines whether the ion concentration of the internal standard liquid is within the set concentration range (S505). If it is within the range, the process proceeds to the flow of the continuous analysis shown in FIG. 5B. If it is out of the range, an alarm is issued (S506) and it is switched to the reagent prepared in the other preparation container and the process returns back to S503 to perform the calibration again. If the concentration of the reagent is significantly different from a design value, it is considered that the reagent is in an irregular device state such as a malfunction of the reagent preparation mechanism, and since there is a possibility that the analysis accuracy is affected, the present device is provided with a concentration value correction/determination unit 473.

Next, the operation during the continuous analysis will be described with reference to the flowchart shown in FIG. 5B. After the calibration, serum, urine, or the like are analyzed as the specimens. Although in the processing flow shown in FIG. 5B, there is a detailed operation which is described as the way in which the step of S203 of FIG. 2A is described by the flowchart shown in FIG. 3 in Embodiment 1, in order to simplify the description, the description of detailed operation is omitted.

Specifically, after the specimen is dispensed into the dilution cup 120 by the dispensing nozzle (not shown), the diluent in the diluent preparation container A451 is dispensed into the dilution cup 120 by using the diluent syringe pump 132 and the specimen is diluted in the set ratio D. In the meantime, the reference electrode liquid is introduced into the flow path of the reference electrode 104 from the reference electrode liquid preparation container A461.

The diluted specimen in the dilution cup 120 is sucked from the sipper nozzle 107 and introduced into the flow paths 1011, 1021 and 1031 of the ion selective electrodes 101, 102 and 103. In the liquid junction unit 121, the reference electrode liquid is brought into contact with the diluted specimen. Each potential difference (electromotive force) between the ion selective electrodes 101, 102 and 103 and the reference electrode 104 is measured by the potential measurement unit 471 (S511).

After the remaining liquid in the dilution cup 120 is sucked up by the vacuum suction nozzle 106 and drained into the waste liquid tank 111, the internal standard liquid in the internal standard liquid preparation container A441 is dispensed into the dilution cup 120. In the meantime, the reference electrode liquid is introduced into the flow path 1041 of the reference electrode 104 from the reference electrode liquid preparation container A461. The electromotive force of each electrode is measured by the potential measurement unit 471 in a state where the internal standard liquid in the dilution cup 120 is sucked from the sipper nozzle 107 and the flow paths 1011, 1021 and 1031 of the ion selective electrodes 101, 102 and 103 are filled up with the internal standard liquid (S512). Further, the remaining liquid in the dilution cup 120 is sucked up by the vacuum suction nozzle 106 and drained into the waste liquid tank 111.

The concentration of the specimen is calculated from the slope sensitivity obtained in S503 and the concentration of the internal standard liquid calculated in S504 by using the following calculation formulas (S513).

(C) Concentration of the Specimen $$CS = CIS \times 10^b \quad \text{(Formula 11)}$$

$$b = (EMFIS - EMFS)/SL \quad \text{(Formula 12)}$$

CS: Concentration of the specimen
EMFS: Measured electromotive force of the specimen The above calculation formulas are basic, and various corrections such as temperature drift and carryover may be added. Further, during the analysis, an operation for refreshing the dilution cup or the flow paths may be performed.

During the analysis, if a user replaces any one of the ion selective electrodes 101, 102 and 103 or the reference electrode 104, replace the electrode replacement detection mechanism (not shown) detects that the electrode is replaced (S514) and the calibration operation will be performed. If the electrode is not replaced, the remaining amount in the reagent preparation container is confirmed by a reagent amount monitor mechanism (not shown) (S515). If the reagent remaining amount is sufficient, the analysis of the specimen is continued, and if it is insufficient, the reagent preparation container is switched. Here, the operation at the time of switching the reagent preparation container will be described.

First, before switching the reagent preparation container, the internal standard liquid in the currently used reagent container, for example, the internal standard liquid preparation container A441, is dispensed into the dilution cup. In the meantime, the reference electrode liquid is introduced into the flow path of the reference electrode 104 from the reference electrode liquid preparation container A461. The potential differences (electromotive forces) between each ion selective electrode 101, 102 and 103 and the reference electrode 104 are measured by the potential measurement unit 471 in a state where the internal standard liquid in the dilution cup 120 is sucked from the sipper nozzle 107 and the flow paths 1011, 1021 and 1031 of the ion selective electrodes 101, 102 and 103 are filled up with the internal standard liquid (S531).

Next, the remaining liquid in the dilution cup is sucked up by the vacuum suction nozzle 106 and drained into the waste liquid tank 111. Next, the reagent is supplied from the other reagent preparation container by switching the electromagnetic valve (S532), and the liquid in the supply flow path is replaced (S533). At this time, in the original reagent preparation container, the remaining reagent is drained by a drainage mechanism (not shown), and new reagent preparation is started. The internal standard liquid in the internal standard liquid preparation container B442 is dispensed into the dilution cup. In the meantime, the reference electrode liquid is introduced into the flow path of the reference electrode 104 from the reference electrode liquid preparation container B462.

Next, the potential differences (electromotive forces) between each ion selective electrode 101, 102 and 103 and the reference electrode 104 are measured by the potential measurement unit 471 in a state where the internal standard liquid in the dilution cup is sucked from the sipper nozzle 107 and the flow paths 1011, 1021 and 1031 of the ion selective electrodes 101, 102 and 103 are filled up with the internal standard liquid (S534). The remaining liquid in the dilution cup is sucked up by the vacuum suction nozzle 106 and drained into the waste liquid tank 111.

Next, the concentration value of the internal standard liquid is calculated by the following formulas, and the concentration value correction/determination unit 473 determines whether the concentration is not abnormal and corrects the concentration value of the internal standard liquid (S535). The slope sensitivity (SL) is the value calculated by Formula 8.

(D) Internal Standard Liquid Concentration Correction $$CIS' = CIS \times 10^c \quad \text{(Formula 13)}$$

$$c = (EMFIS' - EMFIS)/SL \quad \text{(Formula 14)}$$

CIS: Concentration of the internal standard liquid in the currently used preparation container
CIS': Concentration of the internal standard liquid in the preparation container after switching
EMFIS: Electromotive force of the internal standard liquid in the currently used preparation container
EMFIS': Electromotive force of the internal standard liquid in the preparation container after switching Then, the continuous analysis is automatically restarted.

In this concentration correction, since the prepared reagent is measured by the ion selective electrode itself used for the analysis of the specimen, an accurate correction can be performed. Alternatively, the prepared reagent may be analyzed a plurality of times to confirm whether the reagent is prepared in a uniform concentration.

Regarding the above-mentioned concentration correction, the value can also be calculated from the value of the slope sensitivity at the time of the calibration and the value of the electromotive force when the standard liquid of known concentration is measured. The reagent preparation containers may be switched one by one instead of three types at the same time.

In the flow electrolyte concentration measurement device 400 according to this embodiment, to the reagent can be prepared with a concentration error of the reagent within 10%, and since the reagent concentration measurement and the correction are appropriately performed at the timing of the reagent container switching, even if there are some concentration adjustment errors at the time of switching, the analytical value will not be shifted. In this way, although the related device required strict concentration adjustment of the internal standard liquid, since the flow electrolyte concentration measurement device according to this embodiment can absorb some concentration adjustment errors, it is possible to reduce the operator's load and device downtime by using a simple mechanism to prepare the reagent. In this embodiment, the drug substance was in a solid form, but a drug substance in a form of concentrated liquid may also be used. In this case, it is necessary to replace the drug substance supply mechanism for liquid.

COMPARATIVE EXAMPLE

Here, as a comparative example to Embodiment 1 and Embodiment 2, a block diagram of the entire configuration of a conventional flow electrolyte concentration measurement device 600 is shown in FIG. 6 which includes a measurement unit 670. The flow of electrolyte concentration measurement of the conventional device is shown in FIGS. 7A and 7B. The flow of the process at the time of start-up of the device in the related device of FIG. 7A is the same as the processing flow at the time of start-up of the device in FIG. 2A described in Embodiment 1, so they are denoted by the same step numbers, and description thereof is omitted.

In the processing flow of the conventional flow electrolyte concentration measurement device 600 during the continuous analysis shown in FIG. 7B, the flow electrolyte concentration measurement device 600 is significantly different from the flow electrolyte concentration measurement device 100 or 400 described in each embodiment of the invention in that there is no bottle switching unit in the device 600.

Therefore, in the related flow electrolyte concentration measurement device 600 shown in FIG. 7B, the specimen is analyzed during the continuous analysis (S711), and the analysis is stopped (S714) and an alarm is issued (S715) after the analysis of the internal standard liquid is performed (S712) and when it is necessary to replace anyone of the reagent bottles 641, 651 or 661 in the reagent bottle replacement determination step (S713).

When an alarm is issued, the device operator replaces any one of the reagent bottles 641, 651 or 661, and analysis cannot be performed until the calibration is completed, so that the period is the downtime of the device. Therefore, the operation rate of the device is decreased and the operator is bound by the time schedule of the reagent bottle replacement.

An experimental flow for demonstrating a stability of an analytical value of the flow electrolyte concentration measurement device 100 in Embodiment 1 of the invention is shown in FIG. 8. As a comparative experiment, the same experimental flow is performed in the related flow electrolyte concentration measurement device 600 to obtain comparative data.

First, the calibration is performed (S801), and standard serum of three concentrations is analyzed twice (S802). Here, in order to simulate a case where an extreme concentration change occurs due to the replacement of the reagent bottle, it is replaced with the internal standard liquid bottle containing the internal standard liquid with an original concentration of 90%, and the liquid of the supply flow path is replaced (S803). The standard serum is analyzed twice (S804), and after the calibration (S805), the standard serum is analyzed twice again (S806). Here, it is replaced with the bottle containing the internal standard liquid of the original concentration (S807), the liquid replacement is performed, and the standard serum is analyzed twice (S808). After the calibration (S809), the standard serum is analyzed twice again (S810).

The result of the verification experiment performed in the related device is shown in FIG. 9. FIG. 9 shows the measurement results of the Na ion concentrations of the standard serum in terms of high concentration Na ion: 901, medium concentration Na ion: 902, and low concentration Na ion: 903. At the timing of replacing the internal standard liquid bottle (between 2 and 3, and between 6 and 7 on the horizontal axis of FIG. 9), any one of high concentration Na ion: 901, medium concentration Na ion: 902, and low concentration Na ion: 903, changes greatly in concentration. On the other hand, after the calibration ("calibration" in FIG. 9), a constant value is shown regardless of the concentration of the internal standard liquid. In the conventional device, it was confirmed that the calibration is necessary after replacing the internal standard liquid bottle in order to maintain the accuracy of the analytical value.

In a case where the similar experiment is performed in the flow electrolyte concentration measurement device 100 in Embodiment 1 of the invention, the measurement results of the Na ion concentrations of the standard serum, in terms of high concentration Na ion: 1001, medium concentration Na ion: 1002, and low concentration Na ion: 1003, are shown in FIG. 10.

In the flow electrolyte concentration measurement device 100 in Embodiment 1 of the invention, the analytical value (Na-ion concentration) was not affected even when an internal standard liquid is switched to the internal standard liquid having a different concentration (between 2 and 3, and between 6 and 7 on the horizontal axis of FIG. 10). As described above, in the flow electrolyte concentration measurement device 100 in Embodiment 1 of the invention, the reagent concentration measurement and correction are performed appropriately at the timing of bottle replacement, so that the reagent bottle can be automatically switched without affecting the analytical value even if the reagent concentration slightly varies at the time of bottle replacement.

The flow electrolyte concentration measurement device 400 in Embodiment 2 of the invention could also obtain the same stability of the analytical value as that in FIG. 10, which is obtained by the flow electrolyte concentration measurement device 100 in Embodiment 1.

In addition, effects of the device 1101 in Embodiment 1 and the device 1102 in Embodiment 2 are compared with that of the related device 1103 in a table 1100 of FIG. 11. In the related device 1103, the electrodes and reagent bottles are installed when the device is started up, and calibration is performed after the temperature adjustment. The above steps will take about 30 minutes. Thereafter, the device operator replaces the reagent bottle every 8 hours when the reagent runs out, and performs the calibration. The analysis stop time at this time is about 10 minutes. For example, after several thousand tests, an operation similar to the device start-up is performed when the electrodes are replaced. Accordingly, in the related device 1103, the device operator is bound by the reagent replacement schedule for every about eight hours.

Meanwhile, in the device 1101 in Embodiment 1 of the invention, it takes the same time to start up the device as the related device, but the bottle is then automatically switched every eight hours, and the reagent concentration is corrected. Each analysis stop time is about one minute, which is significantly shortened, compared to the related device, and the operation of the device operator is not required during the reagent container switching. Since the device operator can replace the empty bottle at a desired timing until the next eight hours, the burden is significantly reduced.

Further, in the device 1102 in Embodiment 2, the device operator only needs to install electrodes and a drug substance of a reagent when the device is started up, and to implement calibration. During the continuous analysis, a new reagent is automatically prepared, switched, and corrected in a preparation container. The device operator is only required at the timing of electrode replacement and can leave the device for about 30 hours. In addition, since only the drug substance obtained by concentrating a reagent is used, the weight of the reagent is about 1%.

REFERENCE SIGN LIST 100, 400, 600 . . . flow electrolyte concentration measurement device 101 . . . chloride ion electrode 102 . . . potassium ion electrode 103 . . . sodium ion electrode 104 . . . reference electrode 105 pinch valve 106 . . . vacuum suction nozzle 107 . . . sipper nozzle 108 . . . diluent supply nozzle 109 . . . internal standard liquid supply nozzle 110 . . . ion selective electrode unit 111 . . . waste liquid tank 112 . . . vacuum pump 122, 123, 124, 125, 126, 127, 128, 421, 422, 423, 424, 425, 426 . . . electromagnetic valve 131 . . . internal standard liquid syringe pump 132 . . . diluent syringe pump 133 . . . sipper syringe pump 140 . . . internal standard liquid bottle switching unit 141 . . . internal standard liquid bottle A 142 internal standard liquid bottle B 150 . . . diluent bottle switching unit 151 . . . diluent bottle A 152 . . . diluent bottle B 160 . . . reference electrode liquid bottle switching unit 161 . . . reference electrode liquid bottle A 162 . . . reference electrode liquid bottle B 171, 471, 671 . . . potential measurement unit 172, 472, 672 . . . record and calculation unit 173, 473 . . . concentration value correction/determination unit 174, 474, 674 . . . output unit 175, 475, 675 . . . control unit 176, 476, 676 . . . input unit 440 . . . internal standard liquid preparation unit 441 . . . internal standard liquid preparation container A 442 . . . internal standard liquid preparation container B 450 . . . diluent preparation unit 451 . . . diluent preparation container A 452 . . . diluent preparation container B 460 . . . reference electrode liquid preparation unit 461 . . . reference electrode liquid preparation container A 462 . . . reference electrode liquid preparation container B 443, 444, 453, 454, 463, 464 . . . stirring unit 447, 457, 467 . . . drug substance 448, 458, 468 . . . drug substance supply unit 481 . . . pure water supply pump.

The invention claimed is:

1. An electrolyte concentration measurement device, comprising:
   a measurement unit that includes an ion selective electrode, a reference electrode, and a potential measurement unit, and the measurement unit measuring, by the potential measurement unit, a potential difference when an internal standard liquid or specimen is supplied to the ion selective electrode;
   a reagent supply unit that supplies a reagent containing the internal standard liquid to the measurement unit;
   a record and calculation processor configured to process information of the potential difference measured by the measurement unit and obtains an ion concentration of the internal standard liquid or the specimen;
   a concentration value correction/determination processor configured to determine whether the ion concentration of the internal standard liquid, which is obtained by the record and calculation unit, is within a preset value range, and corrects the ion concentration value of the internal standard liquid obtained by the record and calculation unit;
   an output device configured to output a result determined by the concentration value correction/determination unit; and
   a controller that controls the measurement unit, the record and calculation processor, the concentration value correction/determination processor, and the output device, wherein the reagent supply unit includes a bottle storage unit that stores a plurality of bottles, each accommodating a reagent such as the internal standard liquid, for each type of reagent, and a bottle switching unit that detects a remaining amount of the reagent in each of the plurality of bottles stored in the bottle storage unit, switches a bottle in which the remaining amount of the reagent is smaller than a preset amount due to supplying the reagent to the measurement unit, to a bottle in which the remaining amount of the reagent is sufficiently larger than the preset amount, by a bottle that is stored in the bottle storage unit and accommodates the same type of reagent, and supplies the reagent to the measurement unit, and the concentration value correction/determination processor corrects the ion concentration of the internal standard liquid or the specimen obtained by the record and calculation processor after the bottle accommodating the same type of reagent is switched, by using information of the ion concentration of the internal standard liquid or the specimen obtained by the record and calculation processor before the bottle is switched, when a bottle supplying a reagent to the measurement unit is switched among a plurality of bottles accommodating the same type of reagent in the reagent supply unit, and the bottle switching unit in the reagent supply unit a remaining amount of the reagent in each of the plurality of bottles, and a flow path switching unit that switches a flow path of the reagent supplying the reagent to the measurement unit among the plurality of bottles accommodating the same type of reagent based on information of the remaining amount of the reagent in the bottle detected.

2. The electrolyte concentration measurement device according to claim 1, further comprising:
   an alarm that is issued if a reagent bottle to be replaced is not replaced with a new reagent bottle.

3. The electrolyte concentration measurement device according to claim 1, wherein
   a drug substance corresponding to the reagent accommodated in the bottle is supplied by the bottle storage unit, and the electrolyte concentration measurement device further comprises a pure water supply unit that supplies pure water to the bottle, and a stirring mechanism that stirs and mixes the drug substance and the pure water in the bottle in which the drug substance is supplied from the drug substance supply unit and the pure water is supplied from the pure water supply unit.

4. An electrolyte concentration measurement device, comprising:
   a measurement unit that includes an ion selective electrode, a reference electrode, and a potential measurement unit, and the measurement unit measuring, by the potential measurement unit, a potential difference when an internal standard liquid or specimen is supplied to the ion selective electrode;
   a reagent supply unit that supplies a reagent containing the internal standard liquid to the measurement unit;
   a record and calculation processor configured to process information of the potential difference measured by the measurement unit and obtains an ion concentration of the internal standard liquid or the specimen;
   a concentration value correction/determination processor configured to determine whether the ion concentration of the internal standard liquid, which is obtained by the record and calculation unit, is within a preset value range, and corrects the ion concentration value of the internal standard liquid obtained by the record and calculation unit;

an output device configured to output a result determined by the concentration value correction/determination unit; and a controller that controls the measurement unit, the record and calculation processor, the concentration value correction/determination processor, and the output device, wherein the reagent supply unit includes a bottle storage unit that stores a plurality of bottles, each accommodating a reagent such as the internal standard liquid, for each type of reagent, and a bottle switching unit that detects a remaining amount of the reagent in each of the plurality of bottles stored in the bottle storage unit, switches a bottle in which the remaining amount of the reagent is smaller than a preset amount due to supplying the reagent to the measurement unit, to a bottle in which the remaining amount of the reagent is sufficiently larger than the preset amount, by a bottle that is stored in the bottle storage unit and accommodates the same type of reagent, and supplies the reagent to the measurement unit, and the concentration value correction/determination processor corrects the ion concentration of the internal standard liquid or the specimen obtained by the record and calculation processor after the bottle accommodating the same type of reagent is switched, by using information of the ion concentration of the internal standard liquid or the specimen obtained by the record and calculation processor before the bottle is switched, when a bottle supplying a reagent to the measurement unit is switched among a plurality of bottles accommodating the same type of reagent in the reagent supply unit, a reagent bottle replacement mechanism by which a device operator can replace the other reagent bottle with a new reagent bottle while an electrolyte concentration measurement is implemented by using a reagent in one reagent bottle.

5. An electrolyte concentration measurement device, comprising:

a measurement unit that includes an ion selective electrode, a reference electrode, and a potential measurement unit, and the measurement unit measuring, by the potential measurement unit, a potential difference when an internal standard liquid or specimen is supplied to the ion selective electrode;

a reagent supply unit that supplies a reagent containing the internal standard liquid to the measurement unit;

a record and calculation processor configured to process information of the potential difference measured by the measurement unit and obtains an ion concentration of the internal standard liquid or the specimen;

a concentration value correction/determination processor configured to determine whether the ion concentration of the internal standard liquid, which is obtained by the record and calculation unit, is within a preset value range, and corrects the ion concentration value of the internal standard liquid obtained by the record and calculation unit;

an output device configured to output a result determined by the concentration value correction/determination unit; and a controller that controls the measurement unit, the record and calculation processor, the concentration value correction/determination processor, and the output device, wherein the reagent supply unit includes a bottle storage unit that stores a plurality of bottles, each accommodating a reagent such as the internal standard liquid, for each type of reagent, and a bottle switching unit that detects a remaining amount of the reagent in each of the plurality of bottles stored in the bottle storage unit, switches a bottle in which the remaining amount of the reagent is smaller than a preset amount due to supplying the reagent to the measurement unit, to a bottle in which the remaining amount of the reagent is sufficiently larger than the preset amount, by a bottle that is stored in the bottle storage unit and accommodates the same type of reagent, and supplies the reagent to the measurement unit, and the concentration value correction/determination processor corrects the ion concentration of the internal standard liquid or the specimen obtained by the record and calculation processor after the bottle accommodating the same type of reagent is switched, by using information of the ion concentration of the internal standard liquid or the specimen obtained by the record and calculation processor before the bottle is switched, when a bottle supplying a reagent to the measurement unit is switched among a plurality of bottles accommodating the same type of reagent in the reagent supply unit, a drug substance corresponding to the reagent accommodated in the bottle is supplied by the bottle storage unit, and the electrolyte concentration measurement device further comprises a pure water supply unit that supplies pure water to the bottle, and a stirring mechanism that stirs and mixes the drug substance and the pure water in the bottle in which the drug substance is supplied from the drug substance supply unit and the pure water is supplied from the pure water supply unit an ion selective electrode used for prepared reagent concentration determination that measures the reagent when the drug substance and the pure water are finished to be added in the reagent bottle at a constant time interval, and determines whether the reagent is prepared in a uniform concentration.

* * * * *